(12) United States Patent
Fleischmann

(10) Patent No.: US 11,172,923 B2
(45) Date of Patent: Nov. 16, 2021

(54) INSTRUMENT FOR SKIN STRETCHING

(71) Applicant: Biowim Products GmbH, Kirchzarten (DE)

(72) Inventor: Wilhelm Fleischmann, Freiburg (DE)

(73) Assignee: Biowim Products GmbH, Kirchzarten (DE)

(*) Notice: Subject to any disclaimer, the term of this patent is extended or adjusted under 35 U.S.C. 154(b) by 20 days.

(21) Appl. No.: 16/463,719

(22) PCT Filed: Nov. 15, 2017

(86) PCT No.: PCT/EP2017/079341
§ 371 (c)(1),
(2) Date: May 23, 2019

(87) PCT Pub. No.: WO2018/095784
PCT Pub. Date: May 31, 2018

(65) Prior Publication Data
US 2019/0380704 A1    Dec. 19, 2019

(30) Foreign Application Priority Data
Nov. 23, 2016 (DE) .................... 10 2016 122 593.2

(51) Int. Cl.
*A61B 17/04* (2006.01)
*A61B 17/00* (2006.01)

(52) U.S. Cl.
CPC .............. *A61B 17/0482* (2013.01); *A61B 2017/00407* (2013.01)

(58) Field of Classification Search
CPC ............ A61B 17/0206; A61B 17/0293; A61B 17/0482; A61B 17/08; A61B 2017/00407; A61B 2017/081; A61B 90/02
See application file for complete search history.

(56) References Cited

U.S. PATENT DOCUMENTS

| 268,632 | A | 12/1882 | Danforth |
| 583,455 | A | 6/1897 | Bush |

(Continued)

FOREIGN PATENT DOCUMENTS

| DE | 73094 | 8/1892 |
| DE | 4335432 | 4/1995 |

(Continued)

OTHER PUBLICATIONS

Keetenwirk-Praxis, "Neue Musterungsmoglichkeiten," 2: 47-48 (2001).

(Continued)

*Primary Examiner* — Mohamed G Gabr
(74) *Attorney, Agent, or Firm* — Akerman LLP; Peter A. Chiabotti

(57) ABSTRACT

An instrument for stretching the skin comprising an elongate, dimensionally stable guide with at last two modules that are disposed on said guide and comprise anchoring means for securing to the skin, wherein at least one of said modules can be moved on the guide in the longitudinal direction thereof, and a non-return device allows movement thereof in a movement direction and blocks movement thereof in the opposite, reverse direction, said non-return device being able to be inverted in terms of the movement direction and the reverse direction.

8 Claims, 6 Drawing Sheets

(56) References Cited

U.S. PATENT DOCUMENTS

| | | | |
|---|---|---|---|
| 2,450,194 A | 9/1948 | Albert | |
| 2,669,747 A | 2/1954 | Detaranto | |
| 3,825,010 A | 7/1974 | McDonald | |
| 3,971,384 A | 7/1976 | Hasson | |
| 4,073,298 A | 2/1978 | Le Roy | |
| 4,382,441 A | 5/1983 | Svedman | |
| 4,409,968 A | 10/1983 | Drummond | |
| 4,422,451 A | 12/1983 | Kalamchi | |
| 4,430,998 A | 2/1984 | Harvey et al. | |
| 4,641,636 A | 2/1987 | Cotrel | |
| 4,854,304 A | 8/1989 | Zielke | |
| 4,896,680 A | 1/1990 | Hirshowitz | |
| 5,127,412 A | 7/1992 | Cosmetto et al. | |
| 5,176,663 A | 1/1993 | Svedman et al. | |
| 5,203,783 A | 4/1993 | Härle | |
| 5,234,462 A | 8/1993 | Pavletic | |
| 5,263,971 A | 11/1993 | Hirshowitz et al. | |
| 5,291,887 A | 3/1994 | Stanley et al. | |
| 5,374,267 A | 12/1994 | Siegal | |
| 5,441,540 A | 8/1995 | Kim | |
| 5,478,340 A | 12/1995 | Kluger | |
| 5,486,196 A | 1/1996 | Hirshowitz et al. | |
| 5,507,775 A | 4/1996 | Ger et al. | |
| 5,531,790 A | 7/1996 | Frechet et al. | |
| 5,549,640 A | 8/1996 | Fontenot | |
| 5,549,713 A | 8/1996 | Kim | |
| 5,571,138 A | 11/1996 | Blomqvist et al. | |
| 5,584,856 A | 12/1996 | Jameel et al. | |
| 5,589,245 A | 12/1996 | Roell | |
| 5,618,310 A | 4/1997 | Ger et al. | |
| 5,636,643 A | 7/1997 | Argenta et al. | |
| 5,645,081 A | 7/1997 | Argenta et al. | |
| 5,653,699 A | 8/1997 | Reed et al. | |
| 5,662,714 A | 9/1997 | Charvin et al. | |
| 5,723,009 A | 3/1998 | Frechet et al. | |
| 5,733,305 A | 3/1998 | Fleischmann | |
| 5,759,193 A | 6/1998 | Burbank et al. | |
| 5,807,295 A | 9/1998 | Hutcheon et al. | |
| 5,814,067 A | 9/1998 | Fleischmann | |
| 5,893,879 A | 4/1999 | Hirshowitz | |
| 5,928,231 A * | 7/1999 | Klein .................. | A61B 17/823 606/218 |
| 6,010,524 A | 1/2000 | Fleischmann | |
| 6,106,544 A | 8/2000 | Brazeau | |
| 6,120,525 A | 9/2000 | Westcott | |
| 6,142,982 A | 11/2000 | Hunt et al. | |
| 6,254,624 B1 | 7/2001 | Oddsen et al. | |
| 6,315,780 B1 | 11/2001 | Lalonde | |
| 6,398,767 B1 | 6/2002 | Fleischmann | |
| 6,471,715 B1 | 10/2002 | Weiss | |
| 6,733,537 B1 | 5/2004 | Fields et al. | |
| 6,755,052 B1 | 6/2004 | Sytz | |
| 6,755,807 B2 | 6/2004 | Risk et al. | |
| 7,208,006 B2 | 4/2007 | Fleischmann | |
| 7,235,090 B2 | 6/2007 | Buckman et al. | |
| 7,520,872 B2 | 4/2009 | Biggie et al. | |
| 8,092,491 B2 | 1/2012 | Fleischmann | |
| 8,114,124 B2 | 2/2012 | Fleischmann | |
| 8,376,972 B2 | 2/2013 | Fleischmann | |
| 8,430,908 B2 | 4/2013 | Fleischmann | |
| 9,271,730 B2 | 3/2016 | Fleischmann | |
| 2002/0188170 A1 | 12/2002 | Santamore et al. | |
| 2003/0092969 A1 | 5/2003 | O'Malley et al. | |
| 2003/0163160 A1 | 8/2003 | O'Malley et al. | |
| 2003/0176890 A1 | 9/2003 | Buckman et al. | |
| 2003/0225436 A1 | 12/2003 | Fleischmann | |
| 2004/0267309 A1 | 12/2004 | Garvin | |
| 2005/0209574 A1 | 9/2005 | Boehringer et al. | |
| 2006/0247649 A1 | 11/2006 | Rezach et al. | |
| 2007/0156175 A1 | 7/2007 | Weadock et al. | |
| 2007/0191885 A1 | 8/2007 | Fleischmann | |
| 2007/0213714 A1 | 9/2007 | Justis | |
| 2008/0147115 A1 | 6/2008 | O'Malley et al. | |
| 2008/0208251 A1 | 8/2008 | Weadock et al. | |
| 2008/0312685 A1 | 12/2008 | O'Malley et al. | |
| 2009/0227845 A1 | 9/2009 | Lo et al. | |
| 2009/0326578 A1 | 12/2009 | Ewers et al. | |
| 2010/0030260 A1 | 2/2010 | Fleischmann | |
| 2010/0113885 A1 | 5/2010 | McBride et al. | |
| 2011/0009706 A1* | 1/2011 | Abdelgany ........ | A61B 17/0293 600/233 |
| 2013/0282056 A1 | 10/2013 | Fleischmann | |
| 2015/0359598 A1 | 12/2015 | Fleischmann | |

FOREIGN PATENT DOCUMENTS

| | | |
|---|---|---|
| DE | 4342457 | 7/1995 |
| DE | 19832634 | 1/2000 |
| DE | 19844355 | 4/2000 |
| DE | 102 09 122 | 10/2003 |
| EP | 0617152 | 9/1994 |
| EP | 0880953 | 12/1998 |
| EP | 1340461 | 9/2003 |
| EP | 1131024 | 9/2004 |
| EP | 2651313 | 10/2013 |
| FR | 2756722 | 6/1998 |
| FR | 2758711 | 7/1998 |
| GB | 2292526 | 2/1996 |
| JP | H-8502919 | 4/1996 |
| JP | H10-510441 | 10/1998 |
| JP | H11-505149 | 5/1999 |
| JP | 2012-507368 | 3/2012 |
| JP | 2014-504912 | 2/2014 |
| RU | 2 021 765 | 10/1994 |
| RU | 1424809 | 9/1998 |
| SU | 1412751 | 7/1988 |
| SU | 1457906 | 2/1989 |
| WO | 9309727 | 5/1993 |
| WO | 95/16416 | 6/1995 |
| WO | 9526698 | 10/1995 |
| WO | 9608223 | 3/1996 |
| WO | 96/18345 | 6/1996 |
| WO | 0018343 | 4/2000 |
| WO | 01/93771 | 12/2001 |
| WO | 10/092455 | 8/2010 |
| WO | 02087481 | 1/2011 |

OTHER PUBLICATIONS

Wollina et al., "Spacer Fabrics—A Potential Tool in the Prevention of Chronic Wounds," Exog Dermatol, 1: 276-278 (2002).

Hirshowitz et al., "Reconstructions of the tip of the nose and ala by load cycling of the nasal skin and harnessing of extra skin," In: Plast Reconstr Surg, 77:316 (1986).

Melis et al., "Primary skin closure of a large groin defect after inguinal lymphadenectomy for penile cancer . . . ," In: The Jour. of Urology, 159(1): 185-187 (1998).

German Patent Office, "Office Action" issued in German Patent Application No. 10 2016 122 593.2 dated Sep. 14, 2017, document of 13 pages.

World Intellectual Property Organization, "International Search Report," and translation thereof issued on International Patent Application No. PCT/EP2017/079341, dated Feb. 12, 2018, document of 5 pages.

Japanese Patent Office, "Notice of Reasons of Refusal," and English machine translation, issued in Japanese patent application No. 2019-523037, dated May 18, 2021, document of 14 pages.

Japanese Patent Office, "Notice of Reasons of Refusal," and English hand translation, issued in Japanese patent application No. 2019-523037, dated May 18, 2021, document of 12 pages.

* cited by examiner

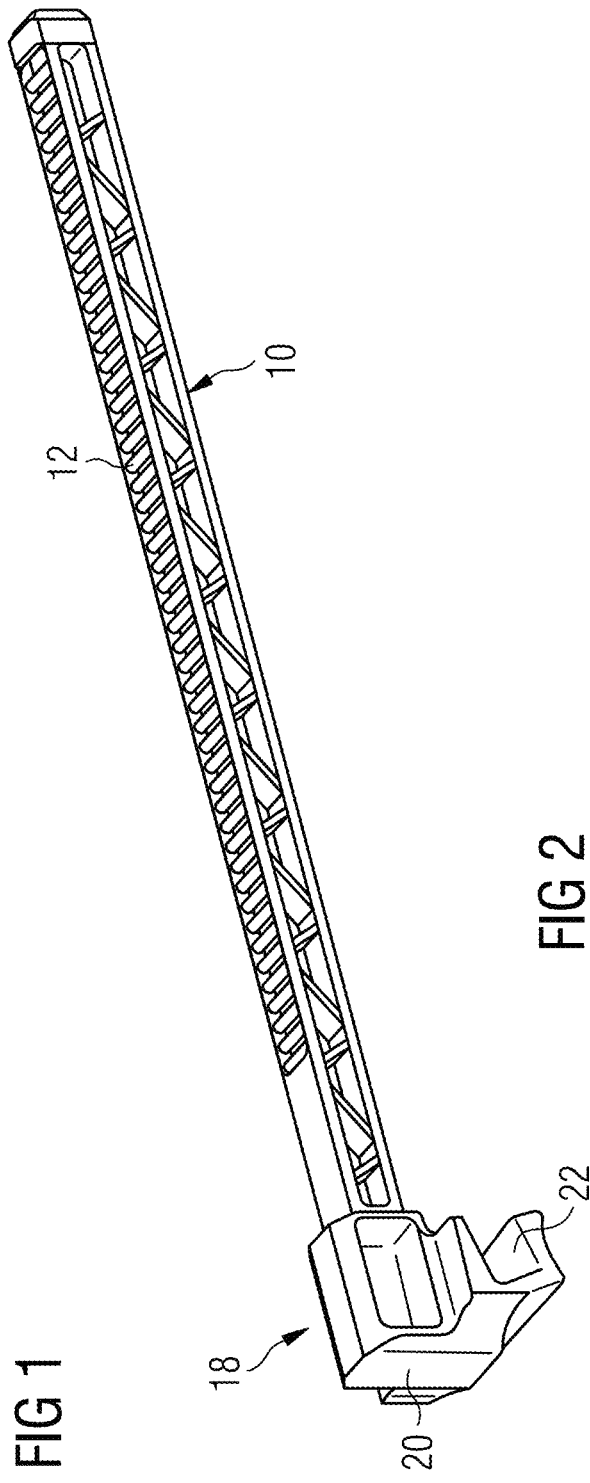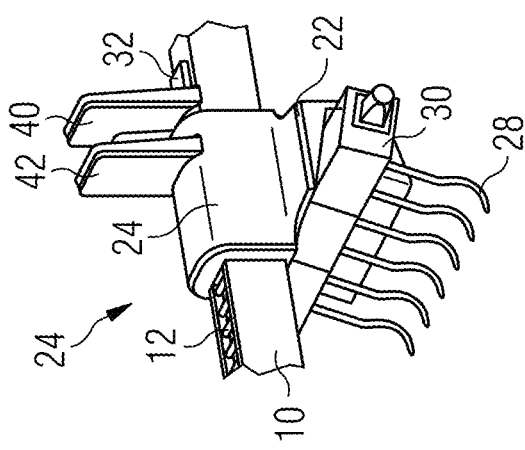

INSTRUMENT FOR SKIN STRETCHING

CROSS REFERENCE TO RELATED APPLICATIONS

This application is a § 371 National Phase of PCT/EP2017/079341, filed Nov. 15, 2017, the entirety of which is incorporated by reference and which claims priority to German Patent Application No. 10 2016 122 593.2, filed Nov. 23, 2016.

FIELD OF APPLICATION

The present application relates to an instrument for stretching the skin.

BACKGROUND

For closing large-area skin defects, it is known to stretch the skin, in particular in the area of the wound edges (skin stretching), to draw the wound edges towards one another. By the tensile force acting on the skin for a defined period of time, it is stretched beyond its natural elasticity limit, with the stretching causing an increase of the skin surface, a redistribution of tissue liquid (anti-edematous effect) as well as an increase of the cell proliferation and matrix synthesis. The surface enlargement of the skin allows the closure of the wound, and the healing thereof is promoted by the stretching-induced stimulation of wound healing.

For this technique of skin stretching, instruments are known wherein at least two modules are disposed on a guide such that they can be moved towards one another. The modules comprise anchoring means, which can be used for securing them each to the skin. At wound edges facing each other, one module each is anchored to the skin. The modules are moved towards one another on the guide to draw the wound edges together. A tensile force stretching the skin is thereby applied to the skin outside the modules. A non-return device allows a movement of the modules in the desired direction for stretching the skin and blocks a movement in the opposite, reverse direction under the elastic tensile force of the stretched skin.

For example, an instrument of this type is known from EP 2 651 313 B1. In this instrument the modules can be displaced along an elongate, dimensionally stable guide. The non-return device is formed by a pawl disposed on the respective module, which engages in a toothing formed at the guide. The toothing is designed as a saw toothing, the obliquely rising tooth flank of which lifts the pawl out of the toothing, when the module is displaced in the desired direction. A reverse movement under the tensile force of the skin is prevented by the pawl running against the respective vertical support surface of the saw teeth. This known instrument is only suitable for drawing the opposing wound edges together.

SUMMARY

The present application discloses embodiments of an instrument that enables a more versatile use for skin stretching.

Accordingly, the present application provides an instrument with the features and structures described herein.

Advantageous embodiments of the present application are further described herein.

In one embodiment, a non-return device is design, where at least one module that can be moved on the guide, such that it is able to be inverted. As a result, the direction of the free movability of the module and the reverse direction, in which the movement of the module is blocked, can each be inverted by 180° so that the movement direction and the reverse direction are interchanged.

It thus becomes possible to apply different stretching effects to the skin using the same instrument. If the non-return device of the movable module is adjusted such that two modules are moved towards one another, the instrument can be used to draw the skin of the wound edges towards one another in a conventional manner. If the non-return device of the movable module is adjusted in the opposite way so that said movable module can only move away from the respective other module, but a movement towards the other module is blocked, the instrument can be used to apply a tensile force to a healthy skin section between these modules stretching and elongating this skin section. This helps to achieve an additional skin gain, which in particular can also be used for wound closure, without the requirement of additional tensile stress of the wound edges.

In an advantageous embodiment of the invertible non-return device, a toothing extending in the longitudinal direction of the guide is designed with ribs extending transversely to the longitudinal direction, which are designed as vertical support surfaces at their two flanks facing in said opposite directions. A pawl disposed at the respective module engages said toothing, the tip of which that engages the toothing is designed with a chamfer facing in the admissible movement direction. When the module moves in the movement direction, the pawl with said chamfer passes over the ribs of the toothing and is lifted out of the toothing by these ribs. In the opposite, reverse direction, the tip of the pawl runs against the vertical support surface of the ribs so that the movement is blocked in the reverse direction. An inversion of the non-return device is achieved by using the pawl with its chamfer rotated by 180° at this module. This may be achieved optionally by disposing two pawls at the module, the chamfered tips of which are directed towards one another by 180°. Depending on the desired movement direction, one pawl is lifted out of the toothing and locked so that this pawl out of order and only the respective other pawl determines the movement direction and the reverse direction.

In a simple embodiment in terms of production the module comprises only one pawl determining the movement direction and the reverse direction. The module can be placed on the guide in two positions rotated by 180°, thereby inverting the direction and the function of the pawl.

If the instrument comprises only two modules, at least one of which is movable and designed with an invertible non-return device, the instrument can on the one hand be used for drawing together wound edges, and on the other hand for stretching a healthy skin area by inverting the non-return device.

With an instrument with at least three modules, additional possible uses are obtained. Two modules, at least one of which is movable and designed with a non-return device, can be moved towards one another to draw the edges of a wound located between these modules together. A third movable module with a non-return device can be disposed on the guide such that it is moved away from the module anchored to the wound edge, thereby stretching the skin outside the wound edge to cause an additional skin proliferation. By inverting the non-return device, the movement can also be enabled in the direction towards the module anchored to the wound edge. An additional tensile force can thus be applied to the skin outside the wound edge causing healthy skin to be pushed towards the wound edge in addition.

In another embodiment, two or more modules are attached to a frame such that the respective orientation of the non-return device can be changed by 180 degrees. Alternatively, a module can also comprise two oppositely oriented pawls, wherein the locking direction is defined by engagement of the respective pawl, as required. The guides can now be drawn through the modules secured to the frame in one movement direction, while the movement in the opposite direction is blocked by the non-return device. By turning the modules secured to the frame by 180 degrees or activating the respective double pawl at the module, the direction of the free movement and the blockage of the respectively assigned guide can be inverted. The advantage of such an embodiment is on the one hand that when moving the wound edges together from the frame, the complete visibility of the wound within the frame is maintained, as no guide crosses the wound. On the other hand, the skin located within the frame can be stretched in two directions (e.g. with a rectangular frame) or even in a circular manner (e.g. with a circular frame) towards the frame, as the guides do not obstruct one another. They are located outside the skin areas intended for stretching, including their possible additional modules and anchoring means. Thus, even if the skin is stretched from the outside towards the frame, there is unrestricted access to the skin area that is stretched, for example, for performing therapeutic or measurement measures.

BRIEF DESCRIPTION OF THE DRAWINGS

In the following, the present application is explained in more detail with reference to the accompanying drawings and illustrated in an exemplary embodiment. In the drawings:

FIG. 1 shows the guide of an instrument according to the present disclosure, FIG. 2 shows a module placed on the guide.

DETAILED DESCRIPTION

In the depicted exemplary embodiment, the instrument for stretching the skin comprises a guide 10 shown as an individual part in FIG. 1. Guide 10 is designed as an elongate rod, preferably made of plastic. Guide 10 has a non-circular, in particular rectangular cross section. Guide 10 is dimensionally stable, i.e. stable against axial tensile and compressive forces as well as bending forces. In the depicted exemplary embodiment, guide 10 is designed as a straight rod. To adapt to the body surface of the patient, the guide can optionally be designed with a longitudinal bend.

Figure 3:
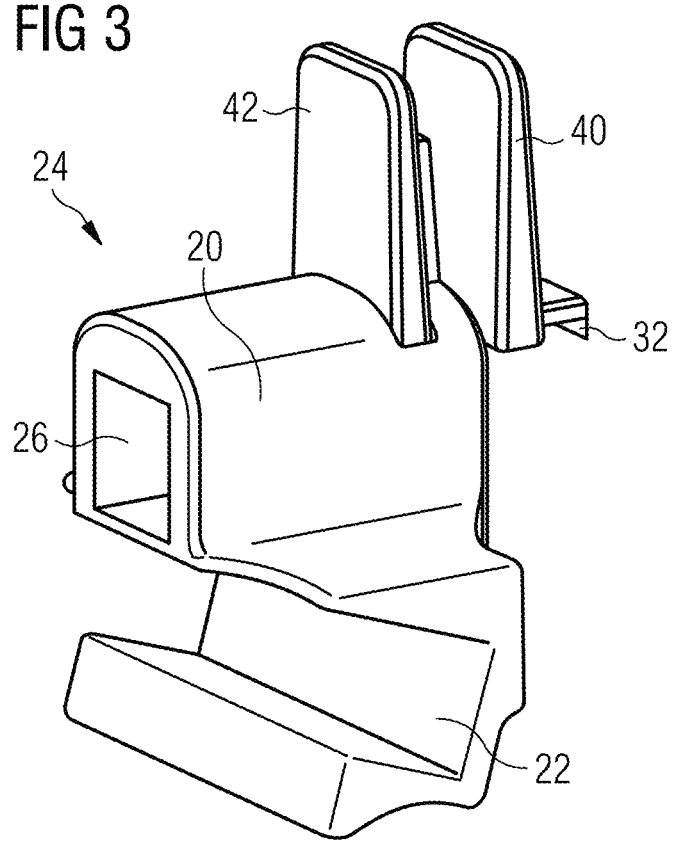
FIG. 3 shows the module in an individual illustration.
Figure 4:
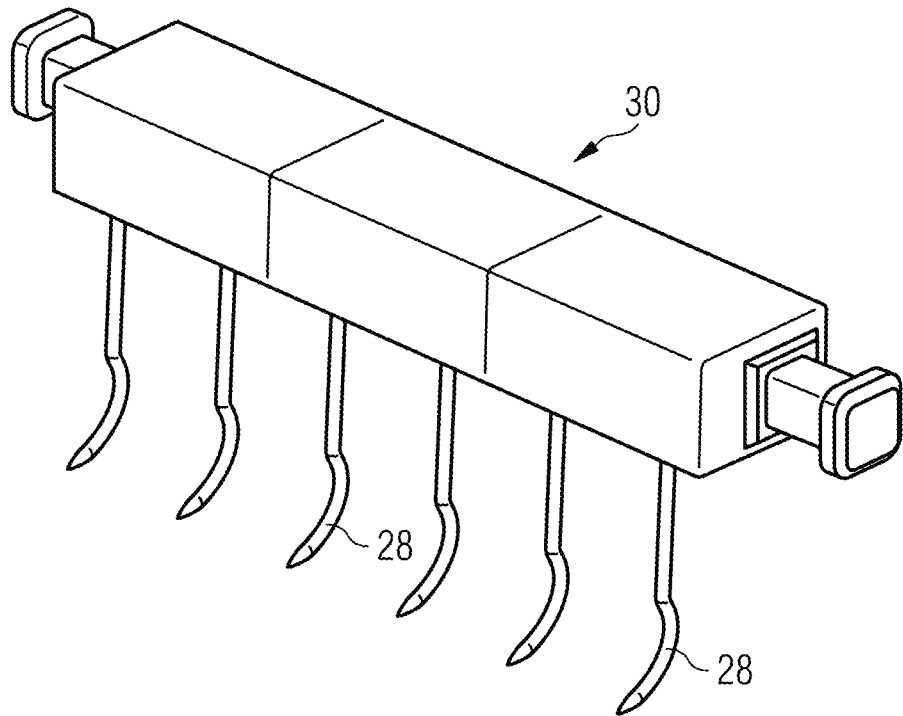
FIG. 4 shows the anchoring means of the module.
Figure 5:
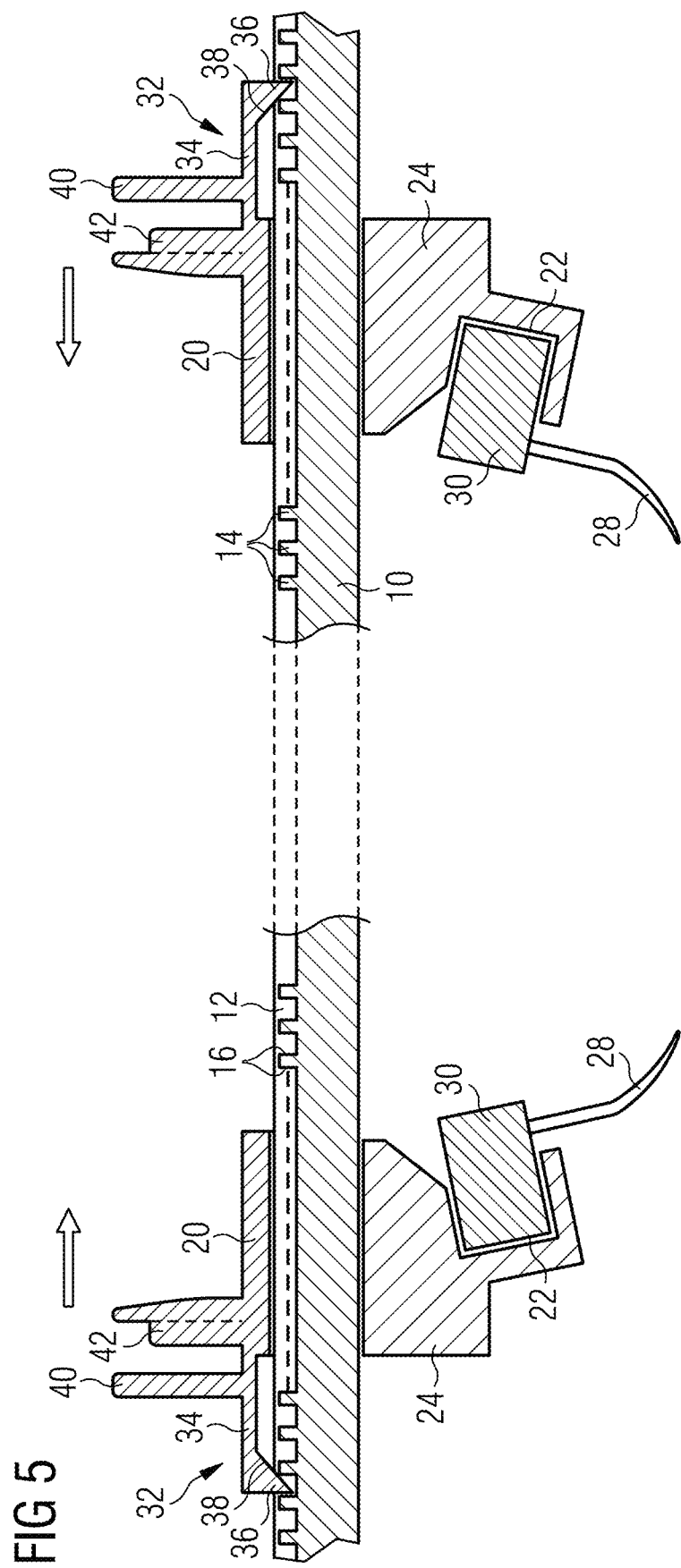
FIG. 5 shows an axial partial section of the instrument with two modules with oppositely directed non-return devices.

At one side surface of guide 10, in FIG. 1 at the top, a toothing 12 is formed, which essentially extends over the entire length of guide 10. As can be seen in FIG. 5, toothing 12 consists of ribs 14 spaced apart in the longitudinal direction of guide 10, which extend transversely to the longitudinal direction of guide 10 and/or toothing 12. In the longitudinal section of guide 10, ribs 14 have an essentially rectangular cross section so that their flanks on both sides form support surfaces 16 each facing the opposite longitudinal directions of guide 10, which essentially extend vertically to the longitudinal axis of guide 10.

As shown in FIG. 1, a module 18 is disposed at the one end of guide 10, which, in the depicted exemplary embodiment, is firmly attached to guide 10, preferably integrally formed of plastic with guide 10. It is understood that module 18 can also be a separate component, which is supported on guide 10. Module 18 may optionally be displaceable on guide 10 and lockable in its position on the guide. Module 18 comprises a module body 20 and a receptacle 22 at the bottom below guide 10, into which the anchoring means can be inserted in a manner described below.

Further, at least a second module 24 is placed on guide 10, the structure of which becomes apparent from FIGS. 2 to 5. The second module 24 comprises a module body 20, which is designed with a continuous perforation 26 in the longitudinal direction, the internal cross section of which corresponds to the external cross section of guide 10. Using this perforation 26, second module 24 can be slid onto guide 10 and is thus guided in an axially displaceable and non-rotatable manner on guide 10. Anchoring means are provided at the bottom of module body 20, which serve for securing module 24 to the skin surface of the patient. In the depicted exemplary embodiment, the anchoring means are needle-shaped hooks 28, which can be inserted into the skin of the patient. At least two hooks 28 are disposed next to each other in a row extending transversally to the longitudinal direction of guide 10 and are supported on a hook support 30, which can be inserted removably into receptacle 22 integrally formed at the bottom of module body 20, as can be seen in FIGS. 2 and 5, in particular. Module 24 and hook support 30 are preferably manufactured from plastic. Hooks 28 are needles made of metal or plastic.

Instead of hooks 28, other anchoring means can also be provided at the bottom of modules 18 and 24 to secure modules 18 and 24 to the skin surface of the patient. Such anchoring means can also be adhesive means or the like, for example. It is essential that the anchoring means allow the introduction of forces into the skin parallel to the surface of the skin.

A pawl 32 is disposed at the end of module body 20 opposite to receptacle 22, above perforation 26. In the depicted exemplary embodiment, pawl 32 is integrally formed with module body 20 as an elastically flexible tongue 34 made of plastic. Tongue 34 protrudes above toothing 12 and parallel thereto from module body 20. The free end of tongue 34 is designed as a tip 36, which protrudes downward from tongue 34 against guide 10 and engages toothing 12, as can be seen in FIG. 5. Tip 36 engaging toothing 12 is formed with a chamfer 38, which extends downward from the bottom of tongue 34 towards tip 36 away from module body 20, as shown in FIG. 5. The width of tongue 34 with tip 36 essentially corresponds to the width of toothing 12 and tongue 34 and is only slightly narrower than toothing 12.

A release lever 40 is integrally formed at the top of tongue 34 and protrudes vertically upward from tongue 34. An integrally formed stop lever 42 protruding upward from module body 20 is assigned to release lever 40. An axial gap remains between release lever 40 and stop lever 42.

Pawl 32 together with toothing 12 forms a non-return device, the function of which becomes apparent from FIG. 5. If module 24 is slid onto guide 10, pawl 32 engages toothing 12 with tip 36, under the elastic spring effect of tongue 34. Tip 36 is located between two consecutive ribs 14. In left-hand module 24 in FIG. 5, the non-return device is directed such that module 24 can be moved to the right on guide 10 (in FIG. 5). Pawl 32 is thereby drawn to the right by module 24. Chamfer 38 passes over rib 14. Pawl 32 is thereby lifted out of toothing 12 and can slide over toothing 12 so that module 24 can be moved freely. If module 24 is moved in the opposite reverse direction (towards the left for left-hand module 24 in FIG. 5), tip 36 of the pawl hits vertical surface 16 of next rib 14 thus blocking the movement of module 24.

According to the present disclosure, the movement direction and the reverse direction of the non-return device can be inverted. To do so, module 24 is slid rotated by 180° onto guide 10, as illustrated in FIG. 5 for module 24 on the right-hand side. In this arrangement, module 24 in FIG. 5 can be moved to the left, wherein pawl 32 passes over toothing 12, while a movement in the reverse direction, i. e. to the right, is blocked. In FIG. 5, the respective movement direction of module 24 relative to guide 10 for both positions is represented by an arrow.

It is understood that in the corresponding operating mode, the non-return device also allows guide 10 to be displaced relative to fixed module 24 in a movement direction and to be blocked in the opposite direction. If, for example, in FIG. 5, left-hand module 24 is fixed, guide 10 can be moved to the left in this left-hand module 24, wherein guide 10 takes the right-hand module 24 along.

If release lever 40 is pushed manually against stop lever 42, release lever 40 pivots tongue 34 upward against the elastic return force thereof and lifts tip 36 out of toothing 12. The non-return device is thereby released and module 24 can be displaced freely on the guide in both directions. This is in particular required to be able to slide module 24 onto guide 10 against the reverse direction of the on-return device, to release the tensile force applied to the skin.

It will be readily appreciated that instead of first module 18 firmly connected to guide 10, a module designed according to second module 24 can also assume the functionality of first module 18. It will further be readily appreciated that in addition to second module 24, a correspondingly designed third module 44 can also be slid onto guide 10, with the movement direction and the reverse direction of second module 24 and third module 44 being able to be inverted independently from one another in any way.

When using hooks 28, it is important to insert these into the skin in the tensile direction, to prevent them from slipping out of the skin under the tensile effect.

In the following, the use of the inventive instrument is explained for various treatment methods.

Figure 6:
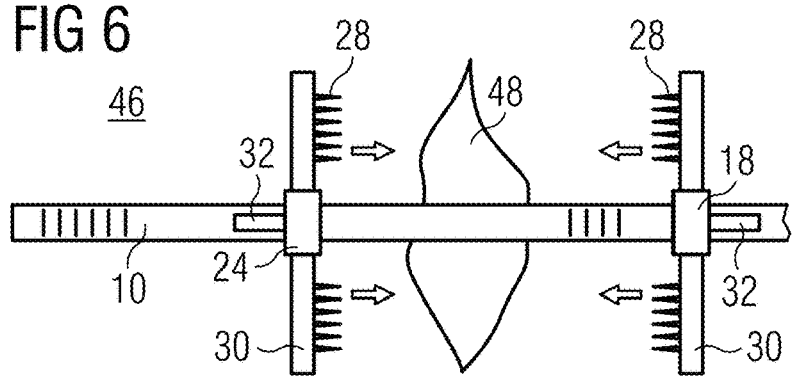
FIGS. 6 to 8 show in a schematic top view various uses of the instrument with two modules.

FIG. 6 shows the use of the instrument for the known method of skin stretching for the purpose of wound closure. This method is preferably used for traumatic skin defects. A first module 18 and a second module 24 are anchored in skin 46 at the two edges of a wound 48 by means of the anchoring means. The two modules 18 and 24 are moved towards one another, as indicated by the arrows, to stretch the skin outside the modules and to draw the edges of wound 48 towards one another, until they can be sutured. The stretching of the skin outside the modules anchored to the wound edges results in a mechanical enlargement of the skin and in a reduction of the tissue edema, which allows the wound edges to be brought together until they can be connected to one another by skin suture.

Figure 7:
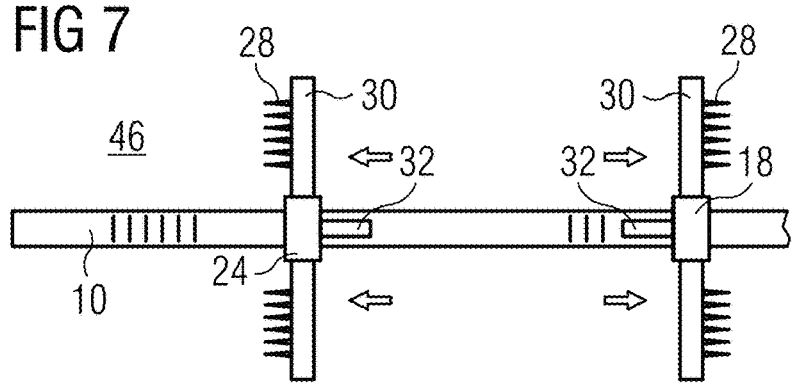

FIG. 7 shows how the two modules 18 and 24 can be moved away from each other by the inventive inversion of the movement direction of module 24, as also indicated by arrows. The undamaged skin 46 between the anchoring points of modules 18 and 24 can thus be temporarily drawn apart. This causes a stretching of the dermal and subdermal cells, which results in a biochemical stimulation of the tissue proliferations and matrix synthesis in addition to the mechanically induced surface enlargement. If high compressive forces are introduced in the skin, a temporary ischemia can be induced, which results in a beneficial hyperfusion upon relaxation of the skin. A controlled damage to the dermal fiber system caused by very high compressive forces activates healing forces, which lead to reconstruction of the fiber system and regeneration of body tissue (remodelling).

Figure 8:
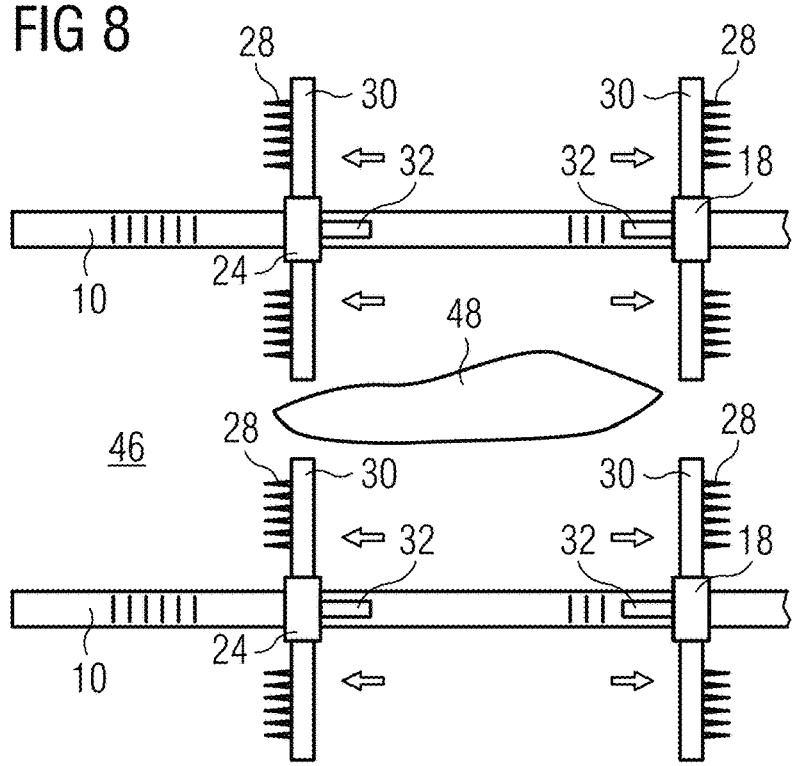

FIG. 8 shows how the skin stretching explained in FIG. 7 can be used for the treatment of a chronic wound 48. Two instruments are anchored to skin 46 at the two sides of a chronic wound, and skin 46 is stretched in these two areas adjacent to the wound by drawing the modules apart. In doing so, a skin injury in the areas adjacent to wound 48 is achieved, which can then be used for closing the wound.

Figure 9:
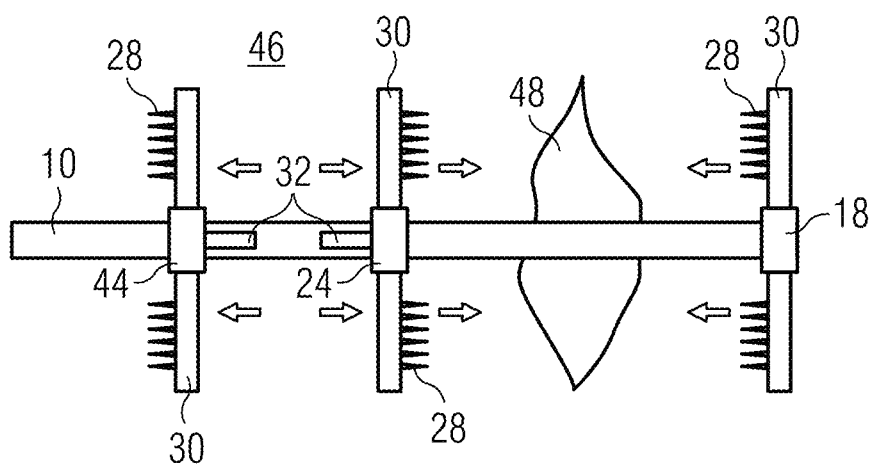
FIGS. 9 and 10 show in a schematic top view various uses of the instrument with three modules.
Figure 10:
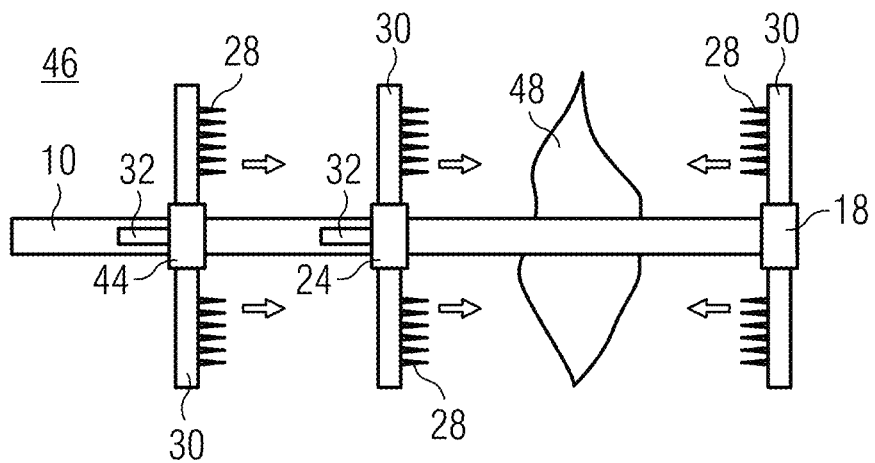

FIGS. 9 and 10 show the use of the instrument with three modules 18, 24 and 44.

In the method shown in FIG. 9, first module 18 and second module 24 are anchored to the skin in the two opposite edges of wound 48. Modules 18 and 24 are moved towards one another to bring the wound edges together. Skin 46 outside modules 18 and 24 is thereby stretched. A third module 44 is placed on guide 10 outside second module 24, with the movement direction and the reverse direction being disposed opposite to second module 24. The skin outside second module 24 can thus be additionally stretched by means of third module 44. This triggers the release of biochemical growth factors in an additional skin area, which initiate and optimize regenerative processes by stimulating tissue regeneration and wound healing (see FIG. 7).

In FIG. 10, first module 18 and second module 24 are also anchored in the two opposite wound edges, to draw these wound edges together. Third module 44 is placed on guide 10 outside second module 24. The movement direction and the reverse direction of third module 44 are directed in the same direction as for second module 24. Third module 44 can thus additionally stretch skin 46 at the side of third module 44 facing away from wound 48 so that the additionally stimulated skin is pushed towards second module 24 and thus towards wound 48 by third module 44.

The present disclosure makes it possible to perform both a wound contraction for closure of a wound and a skin distraction for stimulation of the cell proliferation and matrix synthesis by using the same instrument. In particular, it is also possible to combine these two functions by means of the instrument.

Figure 11:
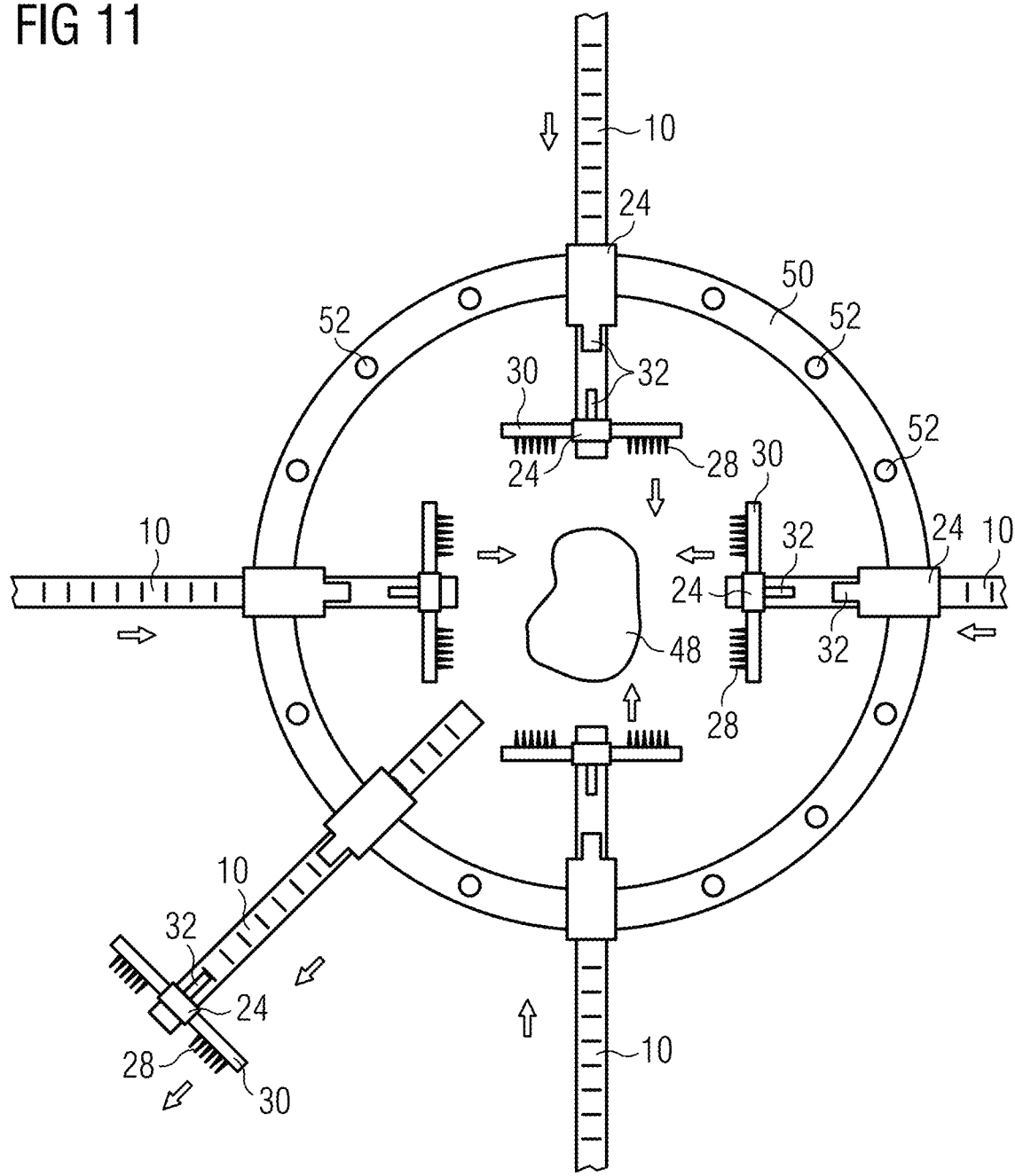
FIG. 11 shows in a schematic top view the use of the instrument with a frame.

Another use of the instrument according to the present disclosure is shown in FIG. 11.

In this embodiment, a rigid frame 50 is used, which is preferably ring-shaped and can have the shape of a rectangle, a polygon or also a circular ring, as can be seen in the drawing. Planar frame 50 comprises a free internal space, in which wound 48 to be treated is located during use. One or several modules 24 can be disposed on frame 50. Preferably, modules 24 are secured to the frame in variable positions. For this purpose, frame 50 may, for example, comprise holes 52 offset from one another by circumferential angles, into which modules 24 are inserted using pins integrally formed at the bottom thereof. In this way modules 24 can be positioned on frame 50 in an invertible arrangement. Guides 10 inserted into modules 24 are thus able to be moved in modules 24 secured to frame 50 relative to modules 24 and frame 50. Depending on the arrangement of modules 24 in frame 50, the non-return device can thus act such that guides 10 can be moved inwards in the movement direction to the internal space of frame 50, while the movement thereof to the outside is blocked. When the non-return device is inverted, a movement of guide 10 to the outside relative to frame 50 is enabled, while the movement to the internal space of frame 50 is blocked.

One or several other modules 24 can be disposed on guides 10. These modules can be designed as modules 18 firmly disposed on the guide or as modules 24 that can be displaced on the guide 10 in one direction by means of a non-return device, as described above.

Due to the different positions of modules 24 on frame 50, the movement directions of guides 10 in these respective modules 24 extend at different angles with respect to one another in the plane of frame 50. As can be seen in FIG. 11, the movement directions can extend at angles of, e.g., 30°, 60°, 90°, 180° etc. Depending on the orientation of the non-return device of respective module 24 secured to frame 50, another module 24 supported on guide 10 within frame 50 can be pushed inward to the internal space of frame 50 and/or a module 24 supported on respective guide 10 outside frame 50 can be radially moved outside away from frame 50. This is indicated in FIG. 11 by respective arrows. If modules 24 disposed within frame 50 are anchored to the skin and moved to the internal space of frame 50 by means of guides 10, the edges of a wound 48 enclosed by frame 50 can be pushed towards one another by these modules 24, to stretch the skin at the edge of wound 48 and to close this wound 48, as, for example, explained in FIGS. 6 and 8. If a second module 24 is disposed on guide 10 outside frame 50 and the non-return device of module 24 secured to frame 50 is positioned such that guide 10 can be moved radially outward, additional stretching of the skin outside frame 50 is possible, to achieve an additional skin gain, as, for example, explained with reference to FIG. 7.

With all these uses, the advantage is obtained that frame 50 and in particular guides 10 with modules 24 are located outside the skin area to be treated and wound 48 and do not impede or restrict the free access to the skin area to be treated and to wound 48. This advantage is preserved, even if several instruments are disposed on frame 50, as, for example, shown in FIG. 11, and skin stretching along the entire circumference of wound 48 with different tensile directions is thus possible.

LIST OF REFERENCE NUMERALS

10 Guide
12 Toothing
14 Ribs
16 Support surface
18 First module
20 Module body
22 Receptacle
24 Second module
26 Perforation
28 Hook
30 Hook support
32 Pawl
34 Tongue
36 Tip
38 Chamfer
40 Release lever
42 Stop lever
44 Third module
46 Skin
48 Wound
50 Frame
52 Holes

The invention claimed is:

1. An instrument for stretching the skin, comprising:
an elongate, dimensionally stable guide with at least two modules that are disposed on the guide with a skin anchoring hook for securing the modules to the skin, wherein at least one of the modules and the guide can be moved relative to one another in a longitudinal direction, and a non-return device allows movement of the at least one of the modules and the guide in a movement direction and blocks movement of the at least one of the modules and the guide in an opposite, reverse direction,
wherein the non-return device is able to be inverted in terms of the movement direction and the reverse direction.

2. The instrument according to claim 1, wherein a third module is disposed on the guide, wherein the third module can be moved relative to the guide and comprises a second non-return device, and wherein the second non-return device is able to be inverted.

3. The instrument according to claim 1, wherein the non-return device comprises:
a toothing formed on the guide and extending in the longitudinal direction of the guide; and
at least one pawl disposed on each of the at least two modules,
wherein the toothing comprising ribs extending transversely to the longitudinal direction, wherein each rib has vertical support surfaces which are disposed vertically to the longitudinal direction at two end faces of the ribs facing in the longitudinal direction,
wherein the pawl engages the toothing with an elastically deflectible free tip, wherein the tip comprises:
a chamfer, which passes over the ribs during movement in the movement direction, thereby lifts the pawl out of the toothing against an elastic return force thereof, and
wherein the tip of the pawl runs against the vertical support surfaces of the ribs during movement in the reverse direction.

4. The instrument according to claim 3, wherein the at least one pawl is disposed at the end of the at least one of the module trailing in the movement direction, and that the at least one of the module can be slid onto the guide in two orientations rotated by 180° to invert the non-return device.

5. The instrument according to claim 1, wherein the non-return device can be rendered inoperable by a release device.

6. The instrument according to claim 5, wherein the release device lifts the pawl out of the toothing against the elastic return force thereof.

7. The instrument according to claim 1, wherein a second guide is disposed on the rigid frame, wherein movement directions of the two guides extend at an angle with respect to one another in a plane of the frame, and wherein a third module disposed on the third guide can be secured to the rigid frame so that the third guide can be moved in its longitudinal direction with respect to the third module and with respect to the frame.

8. The instrument according to claim 7, wherein the frame is a ring-shaped closed frame in one plane enclosing a free inner surface.

\* \* \* \* \*